United States Patent [19]

Zawadzka et al.

[11] Patent Number: 5,543,316
[45] Date of Patent: Aug. 6, 1996

[54] INJECTABLE CULTURE MEDIUM FOR MAINTAINING VIABILITY OF MYOBLAST CELLS

[75] Inventors: Agatha Zawadzka, Charlestown; Wen-Ghih Tsang, Lexington; Robert H. Brown, Needham, all of Mass.

[73] Assignees: Diacrin, Inc., Charlestown; The General Hospital Corporation, Boston, both of Mass.

[21] Appl. No.: 230,334

[22] Filed: Apr. 20, 1994

[51] Int. Cl.$^6$ .................................................. C12N 5/08
[52] U.S. Cl. ........................... 435/240.2; 435/240.3
[58] Field of Search ............................. 435/240.2, 240.3

[56] References Cited

U.S. PATENT DOCUMENTS

| | | | |
|---|---|---|---|
| 5,143,842 | 9/1992 | Ham et al. | 435/240.2 |
| 5,324,656 | 6/1994 | Ham et al. | 435/240.2 |
| 5,328,695 | 7/1994 | Lucas et al. | 424/426 |

OTHER PUBLICATIONS

Mohamed et al., In Vitro, 19(6): 471–8 (1983 Jun.).

Primary Examiner—Michael G. Wityshyn
Assistant Examiner—Jean C. Witz
Attorney, Agent, or Firm—Elliot M. Olstein; Raymond J. Lillie

[57] ABSTRACT

An injectable grade medium for maintaining cells comprising: (a) a sugar; (b) a serum albumin; (c) a calcium salt; (d) a phosphate salt; (e) a source of iron; (f) at least one salt of a Group I element; (g) at least one salt of a Group II element; (h) at least one amino acid; and (i) at least one vitamin. Components (a) through (i) are present in the medium in amounts in order to provide an osmolality of the medium of from about 320 mOsm/kg to about 550 mOsm/kg. Such an injectable grade medium has an increased osmolality as compared with conventional media, and thus such medium may be employed in order to maintain cells over extended periods of time and for injecting such cells into a desired transplantation site of a patient, whereby such cells are transplanted into the patient, and are capable of functioning in the patient.

38 Claims, No Drawings

INJECTABLE CULTURE MEDIUM FOR MAINTAINING VIABILITY OF MYOBLAST CELLS

This invention relates to a culture medium for maintaining the viability of mammalian cells and/or expanding mammalian cells. More particularly, this invention relates to a culture medium for preserving, transporting, maintaining, and expanding mammalian cells, which maintains viability of such cells.

Mammalian cells which may be maintained in a culture medium for the preservation and transport thereof include myoblasts (immature muscle cells) and pancreatic islet cells. Myoblasts may be transplanted into the muscles of a patient suffering from muscular dystrophy or being treated with engineered myoblasts for gene therapy, and pancreatic islet cells may be transplanted into a diabetic patient.

For example, muscular dystrophy is characterized by gradual muscular degeneration, often resulting in death. There are two major types of muscular dystrophy, known is Duchenne muscular dystrophy and Becker muscular dystrophy. Duchenne muscular dystrophy results from a large deletion of the dystrophin gene on the X-chromosome, and Becker muscular dystrophy is the result of one or more point mutations in the same gene. (Hoffman, et al., *N. Engl. J. Med.*, Vol. 318, pgs. 1363–1368 (1988)). Dystrophin is a muscle-specific protein that is localized on the plasma membrane of all muscle cells and is responsible for maintaining cellular integrity during muscle contractions. (Hoffman, et al. *Cell*, Vol. 51, pgs. 919–928 (1987); Koenig, et al., *Cell*, Vol. 53, pgs. 219–228 (1988); Watkins, et al., *Nature*, Vol. 333, pgs. 863–866 (1988)).

Because myoblasts fuse, form a syncytium, and share cytoplasm, it has been postulated that implantation of healthy myoblasts into the muscles of a persons suffering from muscular dystrophy would result in an improvement in the strength of the muscle. (Partridge, et al., *Muscle Nerve*, Vol. 14, pgs. 197–212 (1991)). This may be due to the provision of dystrophin by the healthy myoblasts to intercalated cells or syncytia. Methods have been developed to transplant healthy myoblasts into the muscles of animals or humans suffering from muscular dystrophy. (Huard, et al., *Muscle Nerve*, Vol. 15, pgs. 550–560 (1992); Gussoni, et al., *Nature*, Vol. 356, pgs. 435–438 (1992); Patridge, et al., *Nature*, Vol. 337, pgs. 176–179 (1989)). Inherent in this therapy is the need to obtain a muscle biopsy from a healthy donor, isolate the myoblasts and expand them to provide adequate numbers of cells for transplantation, (Blau, et al., *Proc. Nat. Acad. Sci.*, Vol. 78, pgs. 5623–5627 (1981); Ham, et al., *In Vitro Cell. Dev. Biol.*, Vol. 24, pgs. 833–838 (1988); Law, et al., *Cell Transplantation*, Vol. 2, pgs. 485–505 (1993)). The cells then are administered to the patient by injection.

Following the expansion of the myoblasts, they are transported from the production site to the clinic where they are administered to the patient. The cells must be viable and should be delivered in a medium suitable for injection into a patient.

An example of a medium which was used for myoblast transportation was Dulbecco's phosphate buffered saline to which is added 0.5% human serum albumin. This medium, however, is not a human injectable grade medium. Also, this medium only maintains cell viability for a period of time of from about 2 hours to about 12 hours. Other medium formulations such as saline with 0.5% human serum albumin or Dulbecco's phosphate buffered saline with 25 mM glucose and 0.5% human serum albumin also were ineffective for long-term shipment.

Thus, it is an object of the present invention to provide a medium which provides a greater degree of viability for mammalian cells, and which is an injectable grade medium.

In accordance with an aspect of the present invention, there is provided a medium for maintaining cells. The medium compromises (a) a sugar; (b) a serum albumin; (c) a calcium salt; (d) a phosphate salt; (e) a source of iron; (f) at least one salt of a Group I element; (g) at least one salt of a Group II element; (h) at least one amino acid; and (i) at least one vitamin. Components (a) through (i) are present in the medium in amounts in order to provide an osmolality of the medium of from about 320 mOsm/kg to about 550 mOsm/kg. In accordance with a preferred aspect, the medium is capable of maintaining and transporting cells for over 48 hours at greater than 80% viability and is injectable.

Preferably, the osmolality of the medium is from about 325 mOsm/kg to about 375 mOsm/kg, and more preferably from about 350 mOsm/kg to about 360 mOsm/kg.

The one or more vitamins are preferably present in a total amount of from about 0.02 g/l to about 0.5 g/l, preferably from about 0.03 g/l to about 0.3 g/l.

In one embodiment, the at least one vitamin is one or more vitamins selected from the group consisting of ascorbic acid (Vitamin C); retinol; ergocalciferol; thiamine; riboflavin; pyridoxine; niacinamide; d-pantothenyl alcohol, dl-alpha tocopheryl acetate; biotin; folic acid; and cyanocobalamin. In a preferred embodiment, the medium includes the following vitamins at the following concentrations:

| Vitamin | Concentration (g/l) |
| --- | --- |
| ascorbic acid | 0.132 |
| retinol | 0.00132 |
| ergocalciferol | 0.0000066 |
| thiamine HCl | 0.00396 |
| riboflavin (as riboflavin-5-phosphate sodium) | 0.00475 |
| pyridoxine HCl | 0.00528 |
| niacinamide | 0.0528 |
| d-pantothenyl alcohol; | 0.0198 |
| dl-alpha tocopheryl acetate | 0.0132 |
| biotin | 0.0006 |
| folic acid | 0.004 |
| cyanocobalamin | 0.00005 |

Total vitamin concentration - 0.233 g/l.

In another alternative, the vitamins are included in two groups, Group I and Group II. The vitamins in Group I may be present in the following proportions, with thiamine HCl corresponding to 1.00:

| | |
| --- | --- |
| ascorbic acid | 33.33 |
| retinol | 0.33 |
| ergocalciferol | 0.0017 |
| thiamine HCl | 1.00 |
| riboflavin (as riboflavin-5-phosphate sodium) | 1.20 |
| pyridoxine HCl | 1.33 |
| niacinamide | 13.33 |
| d-pantothenyl alcohol | 5.0 |
| dl-alpha tocopheryl acetate | 3.33 |

The vitamins in Group II may be present in the following proportions, with folic acid corresponding to 1.00:

| | |
|---|---|
| biotin | 0.15 |
| folic acid | 1.00 |
| cyanocobalamin | 0.0125 |

In another embodiment, the at least one amino acid is one or more amino acids selected from the group consisting of isoleucine; leucine; lysine, lysine acetate; methionine; phenylalanine; threonine; tryptophan; valine; alanine; arginine; histidine; proline; serine; glycine; and cysteine.

In a preferred embodiment, the medium has the following amino acids at the following concentrations:

| Amino Acid | Concentration (g/l) |
|---|---|
| isoleucine | 0.0738 |
| leucine | 0.0963 |
| lysine | 0.0775 |
| lysine acetate | 0.1088 |
| methionine | 0.0563 |
| phenylalanine | 0.06 |
| threonine | 0.0425 |
| tryptophan | 0.0163 |
| valine | 0.07 |
| alanine | 0.075 |
| arginine | 0.1013 |
| histidine | 0.03 |
| proline | 0.1188 |
| serine | 0.0625 |
| glycine | 0.1488 |
| cysteine | 0.0018 |
| cysteine HCl x H₂O | 0.0025 |

Total amino acid concentration - 1.1422 g/l.

In another alternative, the amino acids may be present in the following proportions, with tryptophan corresponding to 1.00:

| | |
|---|---|
| isoleucine | 4.53 |
| leucine | 5.90 |
| lysine | 4.75 |
| lysine acetate | 6.67 |
| methionine | 3.45 |
| phenylalanine | 3.68 |
| threonine | 2.61 |
| tryptophan | 1.00 |
| valine | 4.29 |
| alanine | 4.60 |
| arginine | 6.21 |
| histidine | 1.84 |
| proline | 7.29 |
| serine | 3.83 |
| glycine | 9.13 |
| cysteine | 0.11 |
| cysteine HCl x H₂O | 0.15 |

In one embodiment, the sugar is dextrose, which may be present in the medium in an amount of up to about 10 g/l, preferably from about 2.0 g/l to about 8.0 g/l, and more preferably at about 4.5 g/l.

In another embodiment, the serum albumin is human serum albumin. Human serum albumin is present in the medium in an amount of from about 1 g/l to about 10 g/l, preferably at 5 g/l.

In one embodiment, the calcium salt is calcium chloride, present in the medium preferably from about 50 mg/l to about 800 mg/l, more preferably at about 200 mg/l.

The phosphate salt, in one embodiment, is present in the medium in an amount of from about 5 mg P/l to about 100 mg P/l, preferably from about 15 mg P/l to about 25 mg P/l. In one embodiment, the phosphate salt is sodium phosphate.

In yet another embodiment, the at least one salt of a Group I element is selected from the group consisting of sodium bicarbonate and potassium chloride. In one embodiment, both sodium bicarbonate and potassium chloride are present in the medium. Sodium bicarbonate may be present in the medium in an amount of up to about 10 g/l, preferably from about 1 g/l to about 10 g/l, and more preferably at about 3.7 g/l. Potassium chloride may be present in the medium in an amount of up to about 1 g/l, preferably from about 200 mg/l to about 600 mg/l, and more preferably at about 400 mg/l.

In another embodiment, the at least one salt of a Group II element is a magnesium salt. In one embodiment, the magnesium salt is magnesium sulfate. The at least one salt of a Group II metal may be present in an amount of up to about 0.5 g/l, preferably from about 0.19 g/l.

The iron-containing composition is present in the medium in an amount to provide a concentration of iron in the medium up to about 100 μmg/l, preferably from about 5 mg/l to about 20 mg/l, and most preferably at about 14 mg/l.

In a most preferred embodiment, the medium includes the following components in 1 l of aqueous medium in the following amounts:

(a) dextrose—4.5 g/l (25 mM); 9 ml of 50% solution per 1 l of medium;

(b) human serum albumin—5 g/l; 20 ml of 25% solution per 1 l of medium;

(c) sodium bicarbonate—3.7 g/l (44 mM); 44 ml of 8.4% solution per 1 l of medium;

(d) potassium chloride—400 mg/l (5.4 mM); 2.68 ml of 14.9% solution per 1 l of medium;

(e) calcium chloride—200 mg/l (1.8 mM); 2 ml of 10% solution per 1 l of medium;

(f) magnesium sulfate—0.195 g/l (1.625 mM); 0.390 ml of 50% solution per 1 l of medium;

(g) sodium phosphate monobasic and dibasic mix—0.0209 g P/l (0.654 mM P); 0.218 ml of solution containing 96 g P/l per 1 l of medium;

(h) iron—dextran mix 0.000014 g Fe/l (0.00025 mM Fe); 140 μl solution containing 0.1 g Fe/l per 1 l of medium;

(i) amino acids—12.5 ml of 8.5% Travasol Free Amino Acid Solution per 1 l of medium. The amino acids and the concentrations at which they are present in the 8.5% Travasol are as follows:
  isoleucine—5.9 g/l
  leucine—7.7 g/l
  lysine—6.2 g/l
  lysine acetate—8.7 g/l
  methionine—4.5 g/l
  phenylalanine—4.8 g/l
  threonine—3.4 g/l
  tryptophan—1.3 g/l
  valine—5.6 g/l
  alanine—6.0 g/l
  arginine—8.1 g/l
  histidine—2.4 g/l
  proline—9.5 g/l
  serine—5.0 g/l
  glycine—11.9 g/l
  cysteine—0.14 g/l
  cysteine (HClxH₂O)—0.2 g/l
  phosphoric acid 1.15 g/l sodium bisulfite—1 g/l (j) vitamins—The vitamins are contained in two solutions, Solution (i) and Solution (ii). The medium contains 6.6 ml of Solution (i) per liter. The vitamins and the concentrations thereof in Solution (i) are as follows:
ascorbic acid (Vitamin C)—2 g/l
retinol (Vitamin A)—0.2 g/l
ergocalciferol (Vitamin D)—0.001 g/l
thiamine HCl (Vitamin $B_1$)—0.6 g/l
riboflavin (Vitamin $B_2$) as riboflavin-5-phosphate sodium—0.72 g/l
pyridoxine HCl (Vitamin $B_6$)—0.8 g/l
niacinamide—8 g/l
d-pantothenyl alcohol—3 g/l
dl-alpha tocopheryl acetate—2 g/l The medium contains 50 ml of Solution (ii) per liter. The vitamins and the concentrations thereof in Solution (ii) are as follows:
biotin—0.012 g/l
folic acid—0.08 g/l
cyanocobalamin—0.001 g/l The above medium has a osmolality of 358 mOsm/kg. The above medium sometimes is hereinafter referred to as Formula I.

The medium of the present invention is an injectable grade medium; i.e., the medium and cells may be injected into a patient. In addition, the medium has an increased osmolality as compared with the conventional transport media such as Dulbecco's phosphate buffered saline plus human serum albumin. Applicants have discovered that, by providing a medium for maintaining cells which has an increased osmolality, such medium provides for increased viability of cells for an increased amount of time as compared with conventional media.

The invention now will be described with respect to the following example. However, the scope of the present invention is not intended to be limited thereby.

EXAMPLE

Human myoblasts of a concentration of $20 \times 10^6$ cells/ml were placed in Dulbecco's phosphate buffered saline plus 0.5% human serum albumin, or in Formula I mentioned hereinabove at 4° C. Viability of the cells in each medium was measured for 48 hours. The percentage of viable cells in each medium over the 48 hour period is given in Table I below.

| | Viability % | |
|---|---|---|
| Time | Formula I | DPBS + 0.5% HSA |
| 0 | 96.5 | 96.8 |
| 2 hrs. | — | 98.8 |
| 8 hrs. | — | 38.8 |
| 12 hrs. | — | 5.4 |
| 16 hrs. | 98.0 | — |
| 24 hrs. | 96.5 | 3.6 |
| 40 hrs. | 95.4 | — |
| 48 hrs. | 88.8 | — |

As shown hereinabove, myoblast viability was maintained in Formula I at greater than 95% even after 40 hours at 4° C. By comparison, the use of DPBS with 0.5% human serum albumin, which is a standard shipping medium for myoblasts, resulted in almost complete cell death by 24 hours. The excellent long term cell stability with the medium of the present invention avoids the need to transport cells to distant sites in a frozen state which affects the quality of the myoblasts (or other mammalian cells) adversely. Frozen cells must be shipped in non-injectable materials such as dimethylsulfoxide and serum. (Shannon, et al., *Tissue Culture: Methods and Applications*, Kruse, et al., eds., pgs. 712–718, academic Press, New York (1973); Macy, et al., *Biological Handbooks, Cell Biology*, Altman, et al., eds., pg. 46, Federation of American Societies for Experimental Biology, Bethesda, Md. (1976). In addition, the freeze-thaw process reduces the viability of myoblasts and other human cells. Further culturing of the cells at the injection site thus is required to remove the non-injectable materials and bring the cells back to a state of high viability. This requirement of further culturing not only is extremely inconvenient but also may compromise the safety of the myoblasts or other cells due to possible contamination introduced during the culturing process.

The medium of the present invention, however, allows physicians, even at distant sites, to receive and transplant immediately the same quality of cells that could be generated at their intended production site.

It is to be understood, however, that the scope of the present invention is not to be limited to the specific embodiments described above. The invention may be practiced other than as particularly described and still be within the scope of the accompanying claims.

What is claimed is:

1. An injectable composition comprising: (i) myoblasts and (ii) an injectable grade medium for maintaining said myoblasts, said injectable grade medium comprising:
   (a) a sugar;
   (b) a serum albumin;
   (c) a phosphate salt;
   (d) iron;
   (e) at least one salt of a Group I element;
   (f) at least one salt of a Group II element;
   (g) at least one amino acid; and
   (h) at least one vitamin, wherein components (a) through (h) are present in said medium in amounts which provide an osmolality of said medium of from about 320 mOsm/kg to about 550 mOsm/kg, said composition being essentially free of growth factors.

2. The composition of claim 1 wherein said at least one vitamin is present in said medium in a total concentration of from about 0.02 g/l to about 0.3 g/l.

3. The composition of claim 1 wherein said sugar is dextrose.

4. The composition of claim 3 wherein said dextrose is present in said medium in an amount of up to about 10 g/l.

5. The composition of claim 4 wherein said dextrose is present in said medium in an amount of from about 2.0 g/l to about 8.0 g/l.

6. The composition of claim 5 wherein said dextrose is present in said medium in an amount of about 4.5 g/l.

7. The composition of claim 1 wherein said serum albumin is human serum albumin.

8. The composition of claim 7 wherein said human serum albumin is present in said medium in an amount of from about 1 g/l to about 10 g/l.

9. The composition of claim 8 wherein said human serum albumin is present in said medium in an amount of about 5 g/l.

10. The composition of claim 1 wherein said phosphate salt is present in said medium in an amount of from about 5 mg phosphorus/l to about 100 mg phosphorus/l.

11. The composition of claim 10 wherein said phosphate salt is present in said medium in an amount of from about 15 mg phosphorus/l to about 25 mg phosphorus/l.

12. The composition of claim 1 wherein said phosphate salt is sodium phosphate.

13. The composition of claim 1 wherein said at least one salt of a Group I element is selected from the group consisting of sodium bicarbonate and potassium chloride.

14. The composition of claim 13 wherein sodium bicarbonate and potassium chloride are present in said medium.

15. The composition of claim 14 wherein said sodium bicarbonate is present in said medium in an amount up to about 10 g/l.

16. The composition of claim 15 wherein said sodium bicarbonate is present in said medium in an amount of from about 1 g/l to about 10 g/l.

17. The composition of claim 16 wherein said sodium bicarbonate is present in said medium in an amount of about 3.7 g/l.

18. The composition of claim 14 wherein said potassium chloride is present in said medium in an amount up to about 1 g/l.

19. The composition of claim 18 wherein said potassium chloride is present in said medium in an amount of from about 200 mg/l to about 600 mg/l.

20. The composition of claim 19 wherein said potassium chloride is present in said medium in an amount of about 400 mg/l.

21. The composition of claim 1 wherein said at least one salt of a Group II element includes both calcium chloride and magnesium sulfate.

22. The composition of claim 21 wherein said calcium chloride is present in said medium in an amount of from about 50 mg/l to about 800 mg/l.

23. The composition of claim 22 wherein said calcium chloride is present in said medium in an amount of about 200 mg/l.

24. The composition of claim 21 wherein said magnesium sulfate is present in said medium in an amount of up to about 0.5 g/l.

25. The composition of claim 24 wherein said magnesium sulfate is present in said medium in an amount of about 0.19 g/l.

26. The composition of claim 1 wherein said iron is present in said medium to provide a concentration of iron in said medium of up to about 100 μg/l.

27. The composition of claim 26 wherein said iron is present in said medium to provide a concentration of iron in said medium of from about 5 μmg/l to about 20 μg/l.

28. The composition of claim 27 wherein said iron is present in said medium to provide a concentration of iron in said medium of about 14 μg/l.

29. The composition of claim 1 wherein said at least one vitamin is one or more vitamins selected from the group consisting of ascorbic acid; retinol; ergocalciferol; thiamine; riboflavin; pyridoxine; niacinamide; d-pantothenyl alcohol; dl-alpha tocopheryl acetate; biotin; folic acid; and cyanocobalamin.

30. The composition of claim 29 wherein said vitamins are present in said medium at the following concentrations:

| vitamin | concentration (g/l) |
| --- | --- |
| ascorbic acid | 0.132 |
| retinol | 0.00132 |
| ergocalciferol | 0.0000066 |
| thiamine HCl | 0.00396 |
| riboflavin (as riboflavin-5-phosphate sodium) | 0.00475 |
| pyridoxine HCl | 0.00528 |
| niacinamide | 0.0528 |
| d-pantothenyl alcohol | 0.0198 |
| dl-alpha tocopheryl acetate | 0.0132 |
| biotin | 0.0006 |
| folic acid | 0.004 |
| cyanocobalamin | 0.00005. |

31. The composition of claim 29 wherein said vitamins are included in said medium in two groups, Group I and Group II, wherein Group I includes the following vitamins present in said medium in the following proportions, with thiamine HCl corresponding to 1.00:

| | |
| --- | --- |
| ascorbic acid | 33.33 |
| retinol | 0.33 |
| ergocalciferol | 0.0017 |
| thiamine HCl | 1.00 |
| riboflavin (as riboflavin-5-phosphate sodium) | 1.20 |
| pyridoxine HCl | 1.33 |
| niacinamide | 13.33 |
| d-pantothenyl alcohol | 5.0 |
| dl-alpha tocopheryl acetate | 3.33 | and Group II includes the following vitamins present in said medium in the following proportions, with folic acid corresponding to 1.00:

| | |
| --- | --- |
| biotin | 0.15 |
| folic acid | 1.00 |
| cyanocobalamin | 0.0125. |

32. The composition of claim 1 wherein said at least one amino acid is one or more amino acids selected from the group consisting of isoleucine; leucine; lysine;lysine acetate; methionine; phenylalanine; threonine; tryptophan; valine; alanine; arginine; histidine; proline; serine; glycine; and cysteine.

33. The composition of claim 32 wherein said amino acids are present in said medium at the following concentrations:

| amino acid | concentration (g/l) |
| --- | --- |
| isoleucine | 0.0738 |
| leucine | 0.0963 |
| lysine | 0.0775 |
| lysine acetate | 0.1088 |
| methionine | 0.0563 |
| phenylalanine | 0.06 |
| threonine | 0.0425 |
| tryptophan | 0.0163 |
| valine | 0.07 |
| alanine | 0.075 |
| arginine | 0.1013 |
| histidine | 0.03 |
| proline | 0.1188 |
| serine | 0.0625 |
| glycine | 0.1488 |
| cysteine | 0.0018 |
| cysteine (HClxH$_2$O) | 0.0025. |

34. The composition of claim 32 wherein said amino acids are present in said medium in the following proportions, with tryptophan corresponding to 1.00:

| | |
|---|---|
| isoleucine | 4.53 |
| leucine | 5.90 |
| lysine | 4.75 |
| lysine acetate | 6.67 |
| methionine | 3.45 |
| phenylalanine | 3.68 |
| threonine | 2.61 |
| tryptophan | 1.00 |
| valine | 4.29 |
| alanine | 4.60 |
| arginine | 6.21 |
| histidine | 1.84 |
| proline | 7.29 |
| serine | 3.83 |
| glycine | 9.13 |
| cysteine | 0.11 |
| cysteine (HClxH$_2$O) | 0.15. |

35. The composition of claim 1 wherein said medium has an osmolality of from about 325 mOsm/kg to about 375 mOsm/kg.

36. The composition of claim 25 wherein said medium has an osmolality of from about 350 mOsm/kg to about 360 mOsm/kg.

37. An injectable composition comprising: (i) myoblasts and (ii) an injectable grade medium for maintaining said myoblasts, said injectable grade medium including the following components in the following amounts based upon 1 liter of said medium:

(a) dextrose in an amount of 4.5 g/liter;

(b) human serum albumin in an amount of 5 g/l;

(c) sodium bicarbonate in an amount of 3.7 g/l;

(d) potassium chloride in an amount of 400 mg/l;

(e) calcium chloride in an amount of 200 mg/l;

(f) magnesium sulfate in an amount of 0.195 g/l;

(g) a mixture of monobasic and dibasic sodium phosphate which provides 0.0209 g phosphorus/l;

(h) a mixture of iron and dextran which provides 0.000014 g iron/l;

(i) 12.5 ml of an 8.5 % free amino acid solution, said solution including the following amino acids present in the following amounts:
isoleucine—5.9 g/l
leucine—7.7 g/l
lysine—6.2 g/l
lysine acetate—8.7 g/l
methionine—4.5 g/l
phenylalanine—4.8 g/l
threonine—3.4 g/l
tryptophan—1.3 g/l
valine—5.6 g/l
alanine—6.0 g/l
arginine—8.1 g/l
histidine—2.4 g/l
proline—9.5 g/l
serine—5.0 g/l
glycine—11.9 g/l
cysteine—0.14 g/l
cysteine (HClxH$_2$O)—0.2 g/l
phosphoric acid—1.15 g/l
sodium bisulfite—1 g/l (j) 6.6 ml of a first vitamin solution including the following vitamins in the following amounts:
ascorbic acid—20 g/l;
retinol—0.2 g/l;
ergocalciferol—0.001 g/l;
thiamine HCl—0.6 g/l;
riboflavin as riboflavin-5-phosphate sodium—0.72 g/l;
pyridoxine HCl—0.8 g/l;
niacinamide—8 g/l;
d-pantothenyl alcohol—3 g/l;
di-alpha tocopheryl acetate—2 g/l; and (k) 50 ml of a second vitamin solution including the following vitamins in the following amounts:
biotin—0.012 g/l,
folic acid—0.08 g/l,
cyanocobalamin—0.001 g/l,
said medium having an osmolality of 358 mOsm/kg, and said medium being essentially free of growth factors.

38. An injectable composition comprising: (i) myoblasts and (ii) an injectable grade medium for maintaining said myoblasts, said injectable grade medium comprising:

(a) dextrose;

(b) a serum albumin;

(c) a phosphate salt;

(d) iron;

(e) at least one salt of a Group I element;

(f) at least one salt of a Group II element;

(g) at least one amino acid selected from the group consisting of isoleucine;
leucine; lysine; lysine acetate; methionine; phenylalanine; threonine; tryptophan; valine; alanine; arginine; histidine; proline; serine; glycine; and cysteine; and (h) at least one vitamin selected the group consisting of ascorbic acid; retinol; ergocalciferol; thiamine; riboflavin; pyridoxine; niacinamide; d-pantothenyl alcohol; dl-alpha tocopheryl acetate; biotin; folic acid; and cyanocobalamin.

* * * * *